United States Patent [19]
Hudson et al.

[11] Patent Number: 6,043,044
[45] Date of Patent: Mar. 28, 2000

[54] MACROPHAGE MIGRATION INHIBITORY FACTOR AS DIAGNOSTIC AND PROGNOSTIC MARKER FOR METASTATIC ADENOCARCINOMA

[76] Inventors: Perry B. Hudson, 2225 Park St., North, St. Petersburg, Fla. 33710; Said I. Hakky, 8547 Merrimoor Blvd. E., Largo, Fla. 34647-3145; Kathrine Meyer Siegler, 9169 79th Ave., North, Largo, Fla. 33777; A-Hamid Hakki, 8547 Merrimoor Blvd. E., Largo, Fla. 34647-3145

[21] Appl. No.: 08/893,204

[22] Filed: Jul. 15, 1997

[51] Int. Cl.[7] ...................... G01N 33/574; G01N 33/53; G01N 33/537; C12Q 1/68

[52] U.S. Cl. ........................ 435/7.23; 435/6; 435/7.23; 435/7.92; 435/810; 436/64; 536/24.3

[58] Field of Search .................. 436/63, 64, 813; 435/6, 7.23, 7.21, 7.92, 810, 975; 536/24.3

[56] References Cited

U.S. PATENT DOCUMENTS 5,580,726  12/1996  Villeponteau et al. .................... 435/6

OTHER PUBLICATIONS

Meyer–Siegler, et al., *Urology*, vol. 48, No. 3, pp. 448–452, 1996.

*Primary Examiner*—Yvonne Eyler
*Attorney, Agent, or Firm*—Rosenberg, Klein & Lee

[57] ABSTRACT

A method and a kit are provided for the diagnosis and prognosis of human adenocarcinoma. The method and the kit measure levels of macrophage migration inhibitory factor within tumor cells.

11 Claims, No Drawings

MACROPHAGE MIGRATION INHIBITORY FACTOR AS DIAGNOSTIC AND PROGNOSTIC MARKER FOR METASTATIC ADENOCARCINOMA

FIELD OF THE INVENTION

The described invention relates to the diagnosis and prognosis of human adenocarcinoma biopsies. More specifically, this invention uses levels of macrophage migration inhibitory factor within the tumor cells as a measure of metastatic potential and kits for performing the diagnosis.

BACKGROUND OF THE INVENTION

Metastasis, the spread of cancer from a primary site to distant organs, still remains the main cause of death for most cancer patients. Despite years of research, the genetic mechanisms involved in the process are ill defined. Such information is of special importance in cancer prognosis given the uncertain course of the disease. The greatest obstacle to the successful treatment of the cancer patient continues to be the lack of sound prognostic markers, indeed cancer prognosis can not always be accurately assessed using current tumor grading techniques.

The mechanisms which regulate the growth of the cancer cell are of particular relevance to the development of strategies for the treatment of metastatic cancer. Individual patients exhibit extreme variation in cancer progression. In some patients the cancer remains localized, whereas in other the cancer metastasizes quickly. Stromal-epithelial interactions (mediated through cytokine and other growth factors) with the extracellular matrix play a role in development of metastatic cancer.

Using the technique of differential display polymerase chain reaction, it has been found that the cytokine, macrophage migration inhibitory factor (MIF), is one gene whose expression is altered in metastatic prostate cancer when compared to normal tissue (Meyer-Siegler, K. Hudon PB). Enhanced expression of macrophage migration inhibitory factor in prostatic adenocarcinoma metastases. *Urology* 48: 448–452, 1996.

MIF was first described thirty years ago and was designated as a cytokine, a chemical mediator which regulates cell growth by inducing the expression of specific target genes. The initial described function of MIF was as a regulator of inflammation and immunity. However, current research suggests an even greater role for MIF. It is expressed in the brain, and eye lens, is a delayed early response gene in fibroblasts, and it has been reported that this protein can be found in prostate tissues. MIF has been shown to be a pituitary, as well as macrophage cytokine and a critical mediator of septic shock. Recent studies also suggest that MIF may have an autocrine function for embryo development and is produced by the Leydig cells of the testes. Thus, it appears that this cytokine may play a fundamental role in cell growth regulation and possibly development.

SUMMARY OF THE INVENTION

According to the present invention, there is provided a method for the diagnosis of adenocarcinoma and determining the potential metastatic of human cancer. The method is characterized by determining the relative levels of macrophage migration inhibitory factor within tumor cells. The method comprises the steps of obtaining tissue from an individual, extracting ribonucleic acid (RNA) and protein from the tissue and then determine the level of macrophage migration inhibitory factor (MIF). Alternatively, the MIF levels are determined directly in tissue samples.

The method of the invention includes the determination of a 166-bp DNA fragment that is not present in normal prostatic tissue.

In accordance with another embodiment of the invention, there is provided a kit for determining the relative levels of macrophage migration inhibitory factor within tumor cells. The kit comprises: a) a carrier compartmentalized to receive one or more container means therein, b) a first container means comprising oligonucleotide primer for binding cDNA, and c) a second container means comprising ingredients for differential display polymerase chain reaction for amplification of the cDNA.

It is therefore an object of the invention to provide a method for diagnosing cancer.

It is another object of the invention to provide a kit for detecting cancer.

It is a further object of the invention to provide a tumor marker for prostate cancer metastasis.

It is a still further object of the invention to distinguish histological tumors from clinical cancers.

These and other objects and advantages will be better understood from a reading of the description of the preferred embodiments and the claims.

DESCRIPTION OF THE PREFERRED EMBODIMENTS

According to the present invention, there is provided a method of determine the genetic changes associated with the development of metastic tumors, particularly, prostate cancer. The method includes the step of obtaining ribonucleic acid (RNA) from the tissue of an individual and then determine the relative levels of macrophage migration inhibitory factor. The method also provides for the determination of the level of migration inhibitory factor within the tissue sample.

The method further includes the step of determining the presence of a 166-bp DNA fragment.

The determination of the metastatic cancer according to one method is isolate RNA from tissue and using differential display polymerase chain reaction (DD-PCR) techniques with a primer amplifier to identify a 166-bp DNA fragment (D5k) that was not present in normal prostatic tissue. The D5k fragment displays 93% sequence similarity to nucleotides 662 to 845 of the human gene MIF. The sequence of D5k differs from that of human MIF at 11 nucleotides.

According to another embodiment of the invention, there is provided a kit for determining the levels of MIF within tumor cells. The kit comprises: a) a carrier compartmentalized to receive one or more container means therein, b) a first container means comprising oligonucleotide primer for binding cDNA, and c) a second container means comprising ingredients for differential display polymerase chain reaction for amplification of the cDNA.

Preferably, the primer is selected from the group consisting of $T_{12}$ CT(5-dTTTTTTTTTTTTCT-3') and 5'-TGTAGACCCT-3'.

It has now been found that MIF is expressed in the human prostate including pre-pubertal, pubertal, adult normal, benign hyperplastic, focal carcinoma, as well as metastatic prostate tissue samples. It has also been found to be expressed by both normal and cancerous glandular epithelial cells in the human breast, colon, and thyroid.

The over expression of MIF is manifest at both the level of messenger ribonucleic acid (RNA) and protein. It has been found that increased expression of MIF, determined by either messenger RNA levels or biochemical measurement of protein levels using enzyme linked immunosorbent assay (ELISA) and/or immunohistochemical staining intensities (IHC), is associated with human adenocarcinoma (Table 1 and 2). The levels of MIF within prostate tissue can be qualitatively categorized using IHC as weak (pre-pubertal, carcinoma), moderate (pubertal, adult normal and BPH) and strong (metastasis), thus variation in the levels of this protein can serve as a useful prognostic indicator for metastasis (Table 1). The levels of MIF within human breast, thyroid and colon can be qualitatively categorized as weak (normal) or strong (cancer). ELISA analysis can be performed using homogenized tissue that contains variable proportions of epithelial and stromal cells, since significant differences in the levels of MIF protein produced by metastatic tissue when compared with other tissue categories can still be determined (Table 1). An increased content of MIF within epithelial cells is positively correlated with metastasis. Metastatic potential in adenocarcinoma may be predicted by performing biopsies at regular intervals and determining changes in MIF expression levels using ELISA, IHC or messenger RNA levels (Northern, dot blot or reverse transcription PCR). Using this approach the physician can define cancer disease progression and prognosis.

The following examples are given for illustrative purposes only and are not to be construed as limitations upon the scope of the disclosed invention.

EXAMPLE 1

The following studies were performed on fresh or fixed human tissues. In table one the MIF levels were determined by ELISA, IHC, dot blot and Northern analysis. Using ELISA or dot blot analysis the amount of MIF in the metastatic tumor cells is at minimum three times higher than in other cell types (Table 1). In table two the MIF levels were determined by IHC.

TABLE 1

| Category | # of Samples | ELISA reactivity ng/mg total protein | IHC Staining | RNA expression cpm/5 µg RNA |
|---|---|---|---|---|
| Pre-pubertal | 7 | 60.7 +/− 11.3 | 1 | 428 |
| Pubertal | 5 | 182.2 +/− 17.4 | 1–2 | 634 |
| Normal | 5 | 154.0 +/− 15.3 | 2 | 316 |
| BPH | 15 | 162.0 +/− 26.6 | 2 | 521 |
| Carcinoma | 9 | 80.6 +/− 18.6 | 1–2 | 2641 |
| Metastasis | 5 | 490.3 +/− 71.3 | 3 | 8569 |

TABLE 2

| Category | Type | # of Samples | IHC Staining |
|---|---|---|---|
| Breast | Normal | 2 | 1 |
| | Carcinoma | 2 | 3 |
| Colon | Normal | 1 | 1 |
| | Carcinoma | 2 | 1–2 |
| Thyroid | Normal | 1 | 1 |
| | Carcinoma | 2 | 2 |

EXAMPLE 2

Tissue Processing

A. TISSUE FIXATION—Prostate tissue is obtained from patients undergoing surgical operations or needle biopsy. Half of the tissue is fixed in neutral buffered formalin, dehydrated through ethanol and paraffin embedded for immunochemical analysis and the remainder is processed for isolation of RNA and protein.

RNA ISOLATION—RNA is isolated using the TriZOL reagent (Gibco/BRL, Grand Island, N.Y.). 100 mg of tissue is homogenized in the presence of 1 ml of TriZOL reagent using a sterile glass-Teflon homogenizer. The homogenate transferred to a sterile 1.5 ml polypropylene microfuge tube and stored at room temperature for 5 minutes. 200 µl of chloroform is added, the tube shaken by hand for 30 s and then stored at room temperature for 3 minutes. The tube is centrifuged at 12,000 g for 15 minutes. The upper aqueous phase is removed to another tube, the interphase is discarded and the lower organic phase used for protein isolation. The RNA is precipitated by the addition of 500 µl of isopropanol, mixing the tube for 15 s and storing at room temperature for 10 minutes. RNA is pelleted at 12,000 g for 10 minutes at 4° C. The supernatant is removed from the tube, and the RNA pellet is washed with 1 ml of 75% ethanol water. The tube is mixed by vortexing for 30 s and the RNA is pelleted at 7,500 g for 5 minutes at 4° C. The supernatant is removed and the RNA pellet air dried at room temperature for 10 minutes. RNA is dissolved in 100 µl RNase-free water. RNA concentrations and purity are determined by $A_{260/280}$ ratios (Absorbance at 260 nm verses 280 nm).

B. PROTEIN ISOLATION—The lower organic phase from the RNA isolation is transferred to a 2 ml polypropylene microfuge tube. Proteins are precipitated by the addition of 1.5 ml of isopropanol. Samples are mixed by vortexing for 30 s and the incubated at room temperature for 10 minutes. Protein is precipitated at 12,000 g for 10 minutes at 4° C. The protein pellet is washed three times with 2 ml of 0.3M guanidine hydrochloride in 95 ethanol water. After the addition of wash solution the sample is stored at room temperature for 20 minutes and then centrifuged at 7,500 g for 5 minutes at 4° C. The resulting pellet is air dried for 5 minutes and dissolved in 500 µl of distilled water.

C. Enzyme Linked Immunosorbent Assay (ELISA)—For example, 1 µg of total protein, determined using a Bradford microassay (United States Biomedical, Cleveland, Ohio), was plated in 100 µl total volume in 0.05M carbonate-bicarbonate buffer pH 9.6 (Sigma, St. Louis, Mo.). Using human recombinant MIF (R&D Systems, Minneapolis, Minn.) at concentrations ranging from 0.02 to 1 µg/ml in 0.05M carbonate-bicarbonate buffer pH 9.6, a standard curve is generated. All samples and standards are assayed in triplicate. Protein was bound to the plates for 2 hours at 37° C. followed by overnight at 4° C. Plates were washed with PBS containing 0.05% Tween 20 (PBS-T, Sigma) and unoccupied sites in the ELISA wells blocked with 5% bovine serum albumin in PBS-T for 2 hours at 37° C. Primary antibody (goat poly-clonal antibody to human MIF, R&D Systems, Minneapolis, Minn.) is used at a dilution of 1:3,000 in PBS-T and incubated for 1.5 hours at 37° C. Following three washes with PBS-T, secondary antibody (Rabbit-anti-goat alkaline phosphatase conjugate, Sigma) was applied at a 1:30,000 dilution and the plates incubated at 37° C. for 1 hour. Plates were washed again with PBS-T and the substrate, P-nitrophenyl phosphate, disodium (Sigma) added. The color was developed at 37° C. for one hour and the optical density of each well determined at 405 nm using microplate reader (BioTek Instruments, model EL312e, Winooski, Vt.). To quantify MIF levels a standard curve of protein concentration versus absorbance at 405 nm is generated. Metastatic tissue contains levels of MIF at greater than 200 ng/mg total protein.

EXAMPLE 3

Western Blot Analysis

One μg of total protein isolated from tissue is dissolved in 1.5M Tris—HCl, 4% SDS and separated by sodium dodecyl sulphate-polyacrylamide gel electrophoresis using a 10 to 20% tricine pre-cast gel (Novex, San Diego, Calif.). Electrophoresis proceeds at 125 volts constant voltage for 90 minutes using running buffer (0.1M Tris, 0.1M Tricine, 1% SDS pH 8.3). Following electrophoresis, gels are soaked in distilled water for 5 minutes and then soaked in transfer buffer (12 mM Tris, 96 mM glycine in 20% methanol water) for 20 minutes. The resulting electrophoretically separated proteins are transferred to nitrocellulose using 12 mM Tris and 96 mM glycine, pH 8.3 as the transfer buffer. Protein transfer takes 90 minutes using 30 volts constant voltage. Protein blots are washed in distilled water for 15 minutes with shaking and then blocked using 5% Carnation non-fat dry milk in phosphate buffered saline pH 7.4 for 1 hour at 37° C. The blot is incubated with 1 μg/ml of MIF polyclonal antibody (R&D Systems, Minneapolis, Minn.) in PBS-T for 90 minutes at 37° C. Unbound antibody is removed using three 15 minutes washes with PBS-T. Secondary antibody (rabbit anti-goat IgG alkaline phosphatase conjugate, Sigma, St. Louis, Mo.) is added at 1:20,000 dilution in PBS-T for 90 minutes at 37° C. The blot is washed using three 15 minutes washes with PBS-T. Color is developed using 0.15 mg/ml 5-bromo-4-chloro-3-indolyl phosphate, 0.30 mg/ml nitro blue tetrazolium in 100 mM Tris, 5 mM $MgCl_2$, pH 5.0. Color development is stopped by rinsing the blot with distilled water. Band intensity is qualitatively evaluated as 0—absent, 1—weak, 2—moderate, and 3—strong.

EXAMPLE 4

Immunohistochemical Stains

5 μm sections of fixed, paraffin embedded tissue are cut and adhered to poly-L-lysine-coated slides. Tissue sections are deparaffinized by heating to 56° C. for 20 minutes, followed by clearing through three changes of xylene. Tissue is rehydrated by passing through an alcohol series: ten minutes, three charges of each; absolute ethanol, 95% ethanol and 80% ethanol. Tissue is then rinsed in distilled water and rehydrated further in 0.01M phosphate buffered saline pH 7.2 (PBS) for 20 minutes. Endogenous peroxidase activity is quenched by incubating tissue for 30 minutes in 1% hydrogen peroxide in distilled water. Background staining is reduced by incubating sections in 3% bovine serum albumin in PBS for 60 minutes. Primary antibody (goat poly-clonal antibody to human MIF, R&D Systems, Minneapolis, Minn.) is used as the primary antibody at a 1:200 dilution. Primary antibody is added to sections for 60 minutes at 37° C. in a humidified chamber. Negative control slides are treated with goat normal serum in place of the primary antibody at the same concentration. Additional controls omit the primary antibody step. Tissue sections are washed three times for 5 minutes in PBS. Secondary antibody (biotinylated monoclonal anti-goat IgG is then added at a 1:20 dilution in PBS and incubated for 30 minutes at room temperature. Tissue sections are then washed in three charges of PBS for 5 minutes. Extravidin peroxidase is then added at a 1:20 dilution in PBS for 20 minutes at room temperature (ExtrAvidin peroxidase staining kit, Sigma, St. Louis, Mo.). 3,3'-diaminobenzidiene tetrahydrochloride and peroxide (Sigma Fast DAB, Sigma, St. Louis, Mo.) are used as substrates, the reaction monitored and then terminated by rinsing slides with distilled water. Tissue is counterstained using 20% Harris' Hematoxylin for 2 min. MIF IHC staining intensity was qualitatively evaluated as 0—absent, 1—weak, 2—moderate, and 3—strong.

EXAMPLE 5

RNA Blot Analysis

Duplicate 5 μg total RNA samples are bound to nitrocellulose filters using a vacuum manifold. The resulting blots are air dried and the RNA bound to the filter by baking under vacuum for 3 h at 80° C. The blots are then hydrated using sterile distilled water and pre-hybridized for 1 h in RapidHyb buffer (Amersham, Arlington Heights, Ill.) at 65° C. using an Autoblot Microhybridization oven (Bellco, Vineland, N.J.). EcoRI fragments were prepared from a plasmid containing sequenced MIF inserts. These inserts are isolated from low melting point agarose and $32_P$-labeled using the Megaprime DNA random priming kit (Amersham, Arlington Heights, Ill.). 20 μl of the labeled insert is heat denatured (99° C.) and used to probe the slot blot by incubating overnight at 65° C. in Rapid Hyb buffer (Amersham, Arlington Heights, Ill.). Following hybridization unbound probe is removed from the blot with a 20 minute wash using 5×SSC, 0.1% SDS at room temperature. High stringency is achieved by washing the slot blots with two washes using 0.5×SSC, 0.1% SDS at 42° C. for 15 minutes. Washed slot blots are exposed to Kodak XAR-5 film at −80° C. for 24 h. The slot blots are aligned with autoradiographs and the bands excised from the nitrocellulose and quantified by liquid scintillation counting. Prior to slot blot analysis, autolysis is checked in all samples using ethidium bromide staining of 18 S and 28 S rRNA. MIF mRNA levels are higher in both metastatic tissue (30 fold, t—test P<0.01) and focal carcinoma (4 fold higher, t—test P<0.02) when compared with normal prostate tissue samples.

EXAMPLE 6

RT-PCR Analysis

1 μg of total RNA is reverse transcribed using 300 U of Murine Leukemia Virus reverse transcriptase and the protocol as described in the GeneAmp RNA PCR kit (Perkin Elmer, Norwalk, Conn.) using random hexamers as the primer. 5 μl of the resulting cDNA was used as a template in amplification PCR using 2 μM downstream primer 5'-AGCCCACATT-3' and 2 μM upstream primer 5'-TTCATCGTAA-3' (National Biosciences, Plymouth, Minn.) in 50 μl total volume. PCR buffer contain 10 mM Tris—HCl (pH 8.3), 1.5 mM $MgCl_2$ 5 U of AmpliTaq DNA polymerase (PerkinElmer, Norwalk, Conn.) and 0.2 mM of each dNTP. The cycling parameters were 30 sec at 94° C., 55 sec at 40° C. and 30 sec at 72° C. for 40 cycles using a Gene Amp 9600 PCR system (Perkin Elmer, Norwalk, Conn.). PCR products were resolved on 1.5% agarose gels and stained with ethidium bromide. The resulting PCR products are examined by ultraviolet transillumination.

What is claimed is:

1. A method for the diagnosis of adenocarcinoma and determining metastatic ability of human cancer in an individual which comprises the step of determining the increased levels of macrophage migration inhibitory factor within tumor cells.

2. The method of claim 1 wherein tumor cells are derived from tissue.

3. The method of claim 2 wherein said tissue is prostatic tissue.

4. The method of claim 1 including the step of obtaining ribonucleic acid from the tissue of the individual.

5. The method of claim 1 wherein macrophage migration inhibitory factor levels are determined by enzyme linked immunosorbent assay.

6. The method of claim 1 wherein macrophage migration inhibitory factor levels are determined by immunohistochemistry.

7. The method of claim 1 wherein macrophage migration inhibitory factor levels are determined by messenger ribonucleic acid levels.

8. The method of claim 7 wherein macrophage migration inhibitory factor messenger ribonucleic acid levels are determined by reverse transcription polymerase chain reaction.

9. The method of claim 7 wherein macrophage migration inhibitory factor messenger ribonucleic acid levels are determined by Northern blot analysis.

10. The method of claim 1 wherein the macrophage migration inhibitory factor determined comprises a gene fragment having a length of 166 base pairs which is not present in normal prostatic tissue.

11. A kit for determining the level of macrophage migration inhibitory level in cells comprising: a) a carrier compartmentalized to receive one or more container means therein, b) a first container means comprising oligonucleotide primer for binding cDNA; selected from the group consisting of $T_{12}$ CT 5'-dTTTTTTTTTTTTCT-3' and 5'-TGTAGACCCT-3' (SEQ ID NOS: 2 and 1) c) a second container means comprising ingredients for differential display polymerase chain reaction for amplification of the cDNA and means for comparing levels of macrophage migration inhibitory factor so as to determine metastatic ability of human cancer.

* * * * *

SEQUENCE LISTING (1) GENERAL INFORMATION:

(iii) NUMBER OF SEQUENCES:    2

(B) TELEFAX: (410) 461-3067

(2) INFORMATION FOR SEQ ID NO: 1:

(i)   SEQUENCE CHARACTERISTICS:
          (A) LENGTH: 10 base pairs
          (A) TYPE: nucleic acid
          (C) STRANDEDNESS: single
          (D) TOPOLOGY: linear (ii) MOLECULE TYPE: DNA (iii) HYPOTHETICAL: yes (iv) ANTI-SENSE: no (vi) ORIGINAL SOURCE: Synthetic (x) PUBLICATION INFORMATION:
          (A) AUTHORS: Katherine Meyer-Siegler
              Perry Hudson
          (B) TITLE: Enhanced Expression of Macrophage Migration
              Inhibitory Factor in Prostatic Adenocarcinoma
              Metastases
          (C) JOURNAL: Urology
          (D) VOLUME: 48
          (E) ISSUE: 3
          (F) PAGES: 448-452
          (G) DATE: 1996
          (H) RELEVANT RESIDUES IN SEQ ID NO: 1: FROM 1 to 10

(xi) SEQUENCE DESCRIPTION: SEQ ID NO: 1:

TGTAGACCCT                                                          10

(2)  INFORMATION FOR SEQ ID NO: 2:

(i) SEQUENCE CHARACTERISTICS
          (A) LENGTH: 15 base pairs
          (B) TYPE: nucleic acid
          (C) STRANDEDNESS: single
          (D) TOPOLOGY: linear (ii) MOLECULE TYPE: DNA (iii) HYPOTHETICAL: yes (iv) ANTI-SENSE: no (vi) ORIGINAL SOURCE: synthetic (x) PUBLICATION INFORMATION:
          (A) AUTHORS: Katherine Meyer-Siegler
              Perry Hudson
          (B) TITLE: Enhanced Expression of Macrophage Migration
              Inhibitory Factor in Prostatic Adenocarcinoma Metastases
          (C) JOURNAL: Urology
          (D) VOLUME: 48
          (E) ISSUE: 3
          (F) PAGES: 448-452
          (G) DATE: 1996
          (K) RELEVANT RESIDUES IN SEQ ID NO: 2: FROM 1 TO 15

(xi) SEQUENCE DESCRIPTION: SEQ ID NO: 2:

TTTTTTTTTTTTTCT                                                     15